United States Patent [19]
Brainard, II

[11] Patent Number: 6,048,320
[45] Date of Patent: Apr. 11, 2000

[54] INNER EAR DIAGNOSTIC APPARATUS

[76] Inventor: Edward C. Brainard, II, 23 Rogers Dr., Marion, Mass. 02738

[21] Appl. No.: 08/978,197

[22] Filed: Nov. 25, 1997

Related U.S. Application Data

[60] Provisional application No. 60/032,030, Nov. 25, 1996.

[51] Int. Cl.[7] .................................................. A61B 5/00
[52] U.S. Cl. ............................................................ 600/559
[58] Field of Search ................................... 600/559, 549; 73/585, 587

[56] References Cited

U.S. PATENT DOCUMENTS

| | | | |
|---|---|---|---|
| 3,757,769 | 9/1973 | Arguimbau et al. | 600/559 |
| 4,374,526 | 2/1983 | Kemp | 600/559 |
| 4,459,996 | 7/1984 | Teele . | |
| 4,567,881 | 2/1986 | Heller | 600/559 |
| 4,601,295 | 7/1986 | Teele . | |
| 4,688,582 | 8/1987 | Heller et al. | 600/559 |
| 5,546,956 | 8/1996 | Thornton | 600/559 |
| 5,699,809 | 12/1997 | Combs . | |
| 5,738,633 | 4/1998 | Christiansen | 600/559 |
| 5,792,072 | 8/1998 | Keefe | 600/559 |

*Primary Examiner*—Max Hindenburg
*Attorney, Agent, or Firm*—Alan W. Fiedler

[57] ABSTRACT

A system and method for measurement of ear conditions utilizing a test signal. The apparatus includes a wave guide having a proximal and distal end. The distal end is connected to a probe tip, which may be fabricated of a semi-rigid material or rigid material and may further be a material transmissive light. The probe tip is sized so as to fit at least a portion of the probe tip within the ear canal. The wave guide further includes an acoustic energy source disposed substantially at the proximal end for generating a test acoustic wave in response to a source signal. The wave guide further includes an acoustic energy detector, for example a microphone, for detection of reflected acoustic energy and generation of a electrical signal in response. The apparatus is controlled by a processor. The processor is adapted to generate the source signal which will preferably contain pseudo-random noise. The processor is further adapted to receive the detected signal from the acoustic energy detector and to generate an condition signal related to the ear condition in response to the detector signal and the source signal. The condition signal may be utilized to control a video display, a printout device, or any other device capable of conveying to the operator the ear condition. The apparatus may be further adapted to view the car while testing by including a lens at the proximal end and a light source toward the distal end of the wave guide. Also disclosed is a method for measurement of ear conditions.

9 Claims, 14 Drawing Sheets

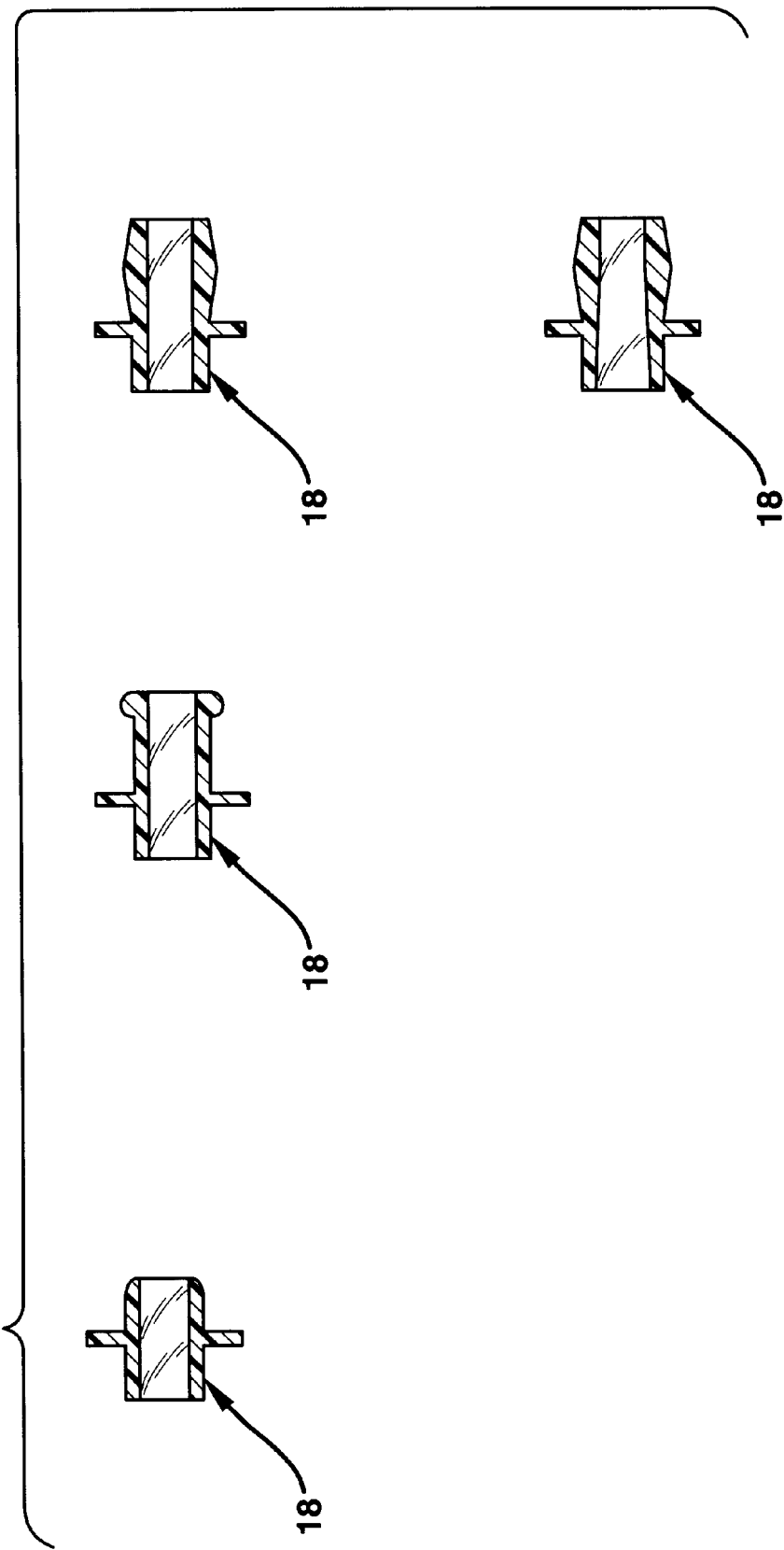

INNER EAR DIAGNOSTIC APPARATUS

CROSS-REFERENCE TO RELATED APPLICATION

This application claims the benefit under 35 U.S.C. §119 (e) of prior provisional application Ser. No. 60/032,030, filed Nov. 25, 1996, which is hereby incorporated by reference.

BACKGROUND OF THE INVENTION

This invention relates to an apparatus for testing and evaluating an individual's capacity to hear and more particularly to an apparatus to monitor middle ear effusion and other ear abnormalities in infants, children and adults.

There are a number of diagnostic tests based upon the use of probes placed within ears to deliver tones and measure the function of the ear elements on a non-contact basis. One method for testing and evaluating auditory responses is impedance audiometry. This method uses acoustical measurements made within the test subject's ear canal. A known acoustic test signal having a predefined frequency is inserted into the ear canal and allowed to propagate to the tympanic membrane. A sensor measures the signal reflected back from the membrane. The impedance of the inner ear is thus computed by comparing the test signal with the reflected signal.

Prior impedance audiometry systems relied on a test probe that sealed to the ear canal, creating a sealed chamber and an air source for selectively pressurizing the chamber. The pressure present in the chamber prestresses the tympanic membrane. At each of a variety of known chamber pressures, these systems would insert the test signal into the ear canal and measure the reflected signal. In this way the inner ear would be characterized by the reflected signals for each of the predetermined pressures.

These prior impedance audiometry systems suffered from a variety of shortcomings. Since the systems require the formation of a sealed chamber between the test probe and the tympanic membrane, the test probe must be adaptable to closely fit a variety of ear canal sizes. In addition, since the system requires the chamber to be pressurized to a pressure value different from atmospheric pressure, the subject can suffer discomfort during testing.

Other diagnostic tests utilize acoustic reflectometry, a test method in which the tool sweeps a range of frequencies at atmospheric pressure without a seal to the ear. The signal reflected from the ear is analyzed and used to generate a test result indicative of the ear condition. The disadvantage with this test method is that measurement of the reflected signal maybe inaccurate due to poor acoustic reflection. In addition, alignment may be off, further degrading instrument performance.

SUMMARY OF THE INVENTION

The present invention is an apparatus or method for detection of ear conditions. In one aspect of the invention, the apparatus includes a wave guide having a proximal and distal end. The distal end is connected to a probe tip, which may be fabricated of a semi-rigid material or rigid material and may further be a material transmissive to light. The probe tip is sized so as to fit at least a portion of the probe tip within the ear canal. In use, the tip may form a seal with the ear canal. The wave guide further includes an acoustic energy source disposed substantially at the proximal end for generating a test acoustic wave in response to a source signal. The wave guide further includes an acoustic energy detector, for example a microphone, for detection of reflected acoustic energy and generation of an electrical signal in response.

The apparatus is controlled by a processor. The processor is adapted to generate the source signal which will preferably contain pseudo-random noise. The processor is further adapted to receive the detected signal from the acoustic energy detector and to generate a condition signal related to the ear condition in response to the detected signal and the source signal. The condition signal may be utilized to control a video display, a printout device, or any other device capable of conveying to the operator the ear condition.

Another aspect of the invention is an apparatus adapted to view the ear while testing using acoustic reflectance. The apparatus may include a lens at the proximal end and a light source toward the distal end of the wave guide. The light source illuminates the ear canal and tympanic membrane either by direct illumination or by transmission of light via the light transmissive probe tip. The lens focuses the light for the operator.

Another aspect of the invention is a probe tip for an acoustic reflectometer, the probe tip may have the portion disposed within the ear canal and have a substantially tapered cross-section. This allows the use of single probe tip over a variety of ear canal sizes.

The apparatus may be contained in a single, hand-held portable device. Alternatively the processor, display devices and power source may be external to the housing.

BRIEF DESCRIPTION OF THE DRAWINGS

A preferred embodiment of the invention has been chosen for purposes of illustration and description and is shown in the accompanying drawings, forming a part of the specification, wherein:

FIG. 3b shows cross-sectional views of a variety of embodiments for the probe tip of the present invention:

DETAILED DESCRIPTION OF THE PREFERRED EMBODIMENT

The present invention is an instrument and method that provides information about the function and integrity of the ear. The instrument monitors middle ear effusion and other ear abnormalities in infants, children and adults. It uses a test probe which couples to the ear at atmospheric pressure and delivers a known test signal.

Figure 1:
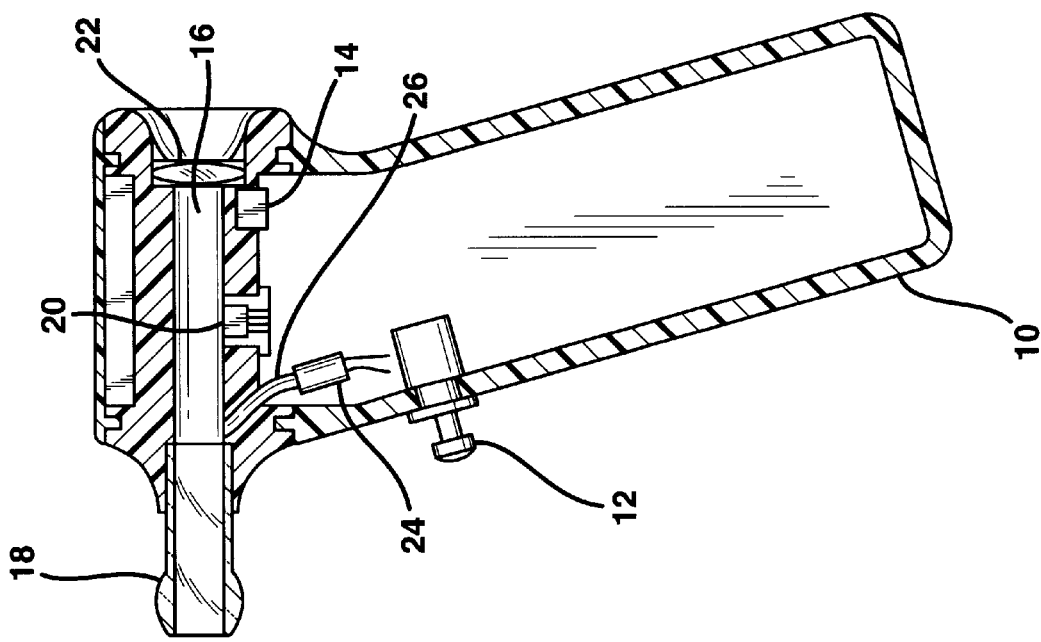
FIG. 1 is a cross-sectional view of an embodiment of the present invention.

FIG. 1 illustrates a cross-sectional view of an embodiment of the present invention. The instrument comprises a housing 10 sized to be held by the clinician. The housing 10 contains a switch 12 for operation of the instrument by the clinician. The switch 12 is adapted to actuate the instrument, wherein a test signal generated by sound source 14 is carried via wave guide 16 to probe tip 18. Probe tip 18 is sized appropriately to fit the test subject. Microphone 20 measures the reflected signal received back from the test subject via probe tip 18 and wave guide 16.

The housing also optionally may include a lens 22 for the clinician to utilize to examine the subject's tympanic membrane. The light source 24 may be positioned as needed and may provide direct illumination, or alternatively, may provide indirect illumination that is then carried to the wave guide 16 via optical fiber 26. Housing 10 also may hold the electronics for performing signal analysis. As an alternative, the control electronics may be exterior to the housing 10 with the control signal for the sound source 14 and the signal detected by the microphone 20 provided externally via wires or optical fibers.

Figure 2:
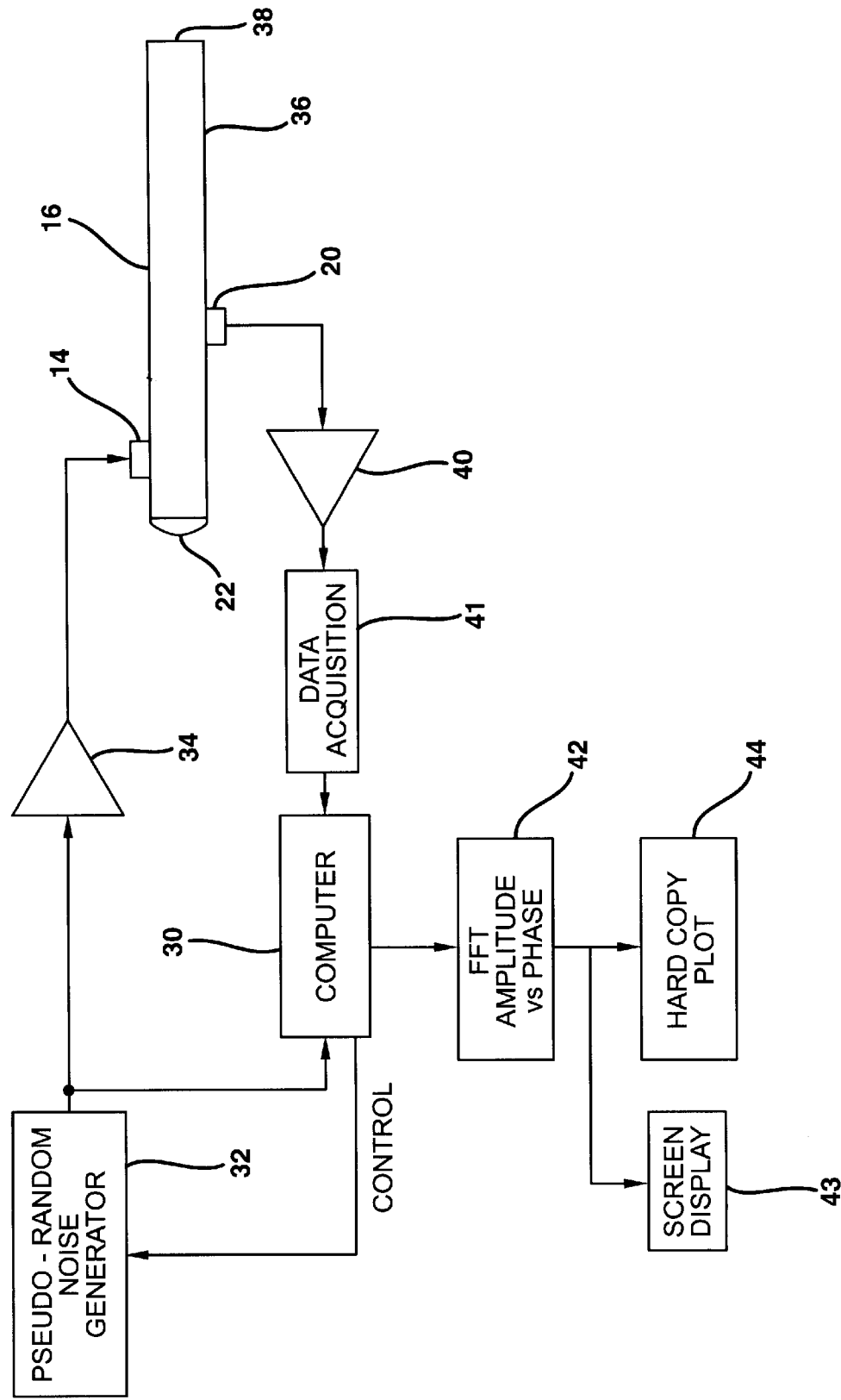
FIG. 2 is a block diagram of the major components of an embodiment of the present invention.

FIG. 2 illustrates a block diagram for an embodiment of the present invention. The system utilizes a computer 30 which may be a digital microcomputer or analog computer. The computer 30 is adapted to control a signal generator 32 to create a test signal. The test signal is preferably pseudo-random noise. The test signal is provided to a power amplifier 34 which amplifies and conditions the signal properly for sound source 14. The sound source 14 creates acoustical energy in response to the input signal. The sound source 14 is placed within the wave guide 16 so that the acoustic energy is passed through the wave guide into the ear canal 36 and onto the tympanic membrane 38. In response to the acoustic energy, a wave is reflected from the tympanic membrane 38 back through the ear canal 38 and into the wave guide 16. This reflected wave is detected by microphone 20 and, in response to the detected reflected wave, generates a signal. The signal is passed through an amplifier 40 and back to the computer 30 through a data acquisition circuit 41 for analysis. The device is first operated in air, the results of which are then subtracted from subsequent readings to provide zeroing at all frequencies.

The computer 30 is further adapted to perform signal analysis on the reflected wave signal with the respect to test signal. For instance, as illustrated, a Fourier Transform function 42 may be performed on the reflected wave signal and plotted on a hard copy device 44 or display on a screen 43. Other forms of signal analysis are possible and known in the art.

Figure 3:
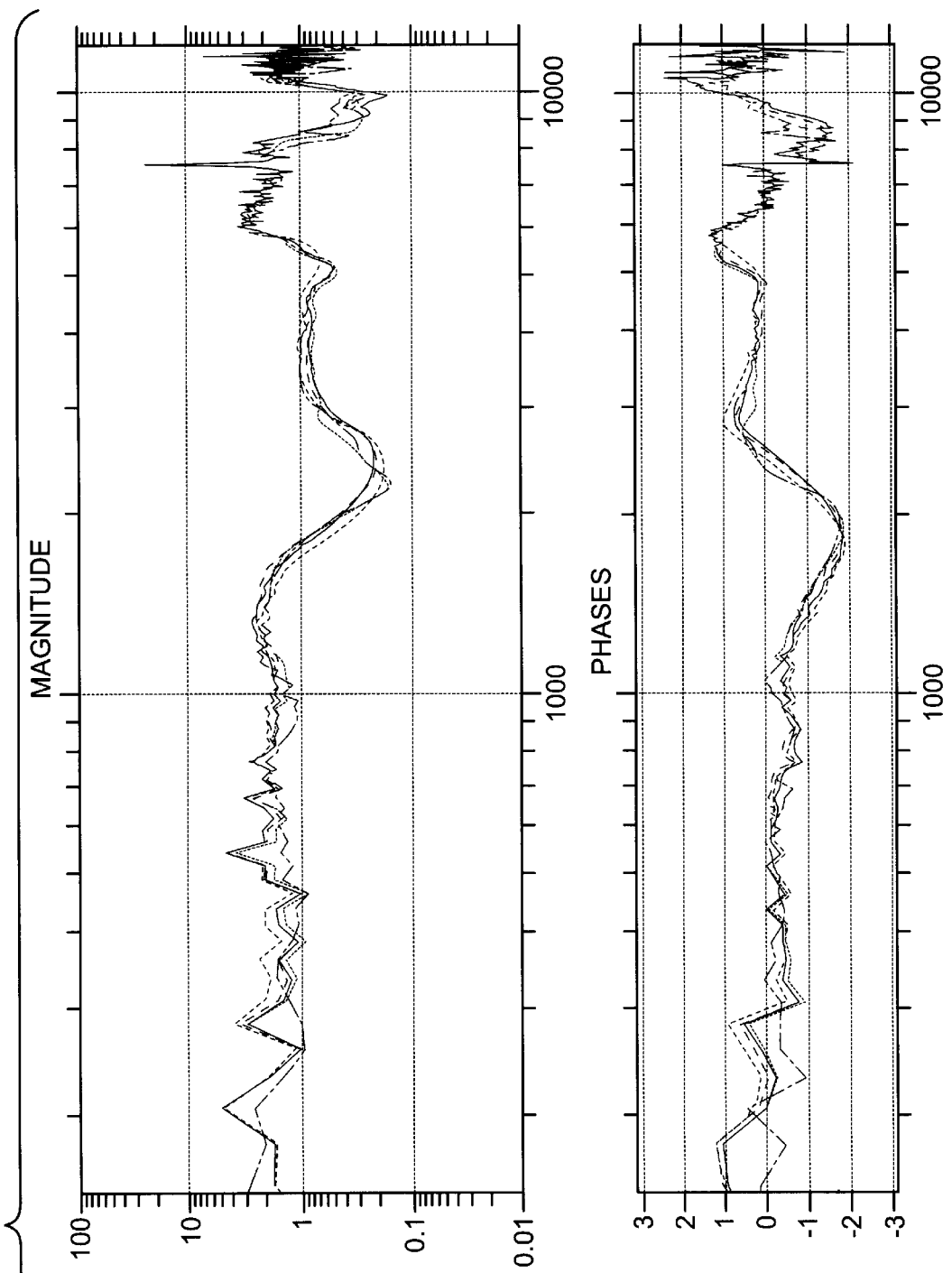
FIG. 3 are graphs illustrating the acoustic measurements utilizing a method of the present invention and indicates the typical response for a normal child ear.

The graphs of FIG. 3 illustrate a typical response from a subject after the instrument has been zeroed in air without any further processing.

FIG. 3b illustrates the design and sizes for a variety of probe tips 18. FIG. 3c illustrates an alternative embodiment of the probe tip 18 wherein the probe tip 18 is designed to be used for a variety of ear canal diameters.

The outside diameter of the tip 18 is selected to penetrate into the ear of a subject and provide an airtight seal so that the instrument and ear canal will be sealed at atmospheric pressure. Thus the unit operates by forming a resonant closed end traveling wave tube to provide greatest selectively and noise rejection. Typical Q for the system is four. This calculation is derived in the following way:

Q of a tuned circuit is Q=$\underline{X}$, where Q=quality factor, X=reactance of either coil or capacitor in ohms, and R=series resistance in ohms.

$$Q = \frac{2\pi(\text{Energy stored/cycle})}{(\text{Energy dissipated/cycle})}$$

$$\text{Bandwidth} - 3dB = \frac{fo}{Q} \text{ and } Q = \frac{fo}{2\Delta f(-3dB)}, \text{ where}$$

fo=the resonant frequency, and
Q=the circuit Q.
High Q means higher selectivity and elimination of noise. Resistance on the equivalent circuit reduces Q.
Given fo=2600 Hz, and
$f_H$=2850 Hz, and
$f_L$=2200 Hz, then $\Delta f$=2850–2200=650.

$$\text{Therefore, } Q = \frac{fo}{\Delta f} = \frac{2600}{650} = 4.$$

Two different tip sizes are required to monitor from infants to grown children. The tips are designed so that a characteristic acoustic signature is detected by the instrument to allow automatic calibration adjustment for different tips.

Figure 4:
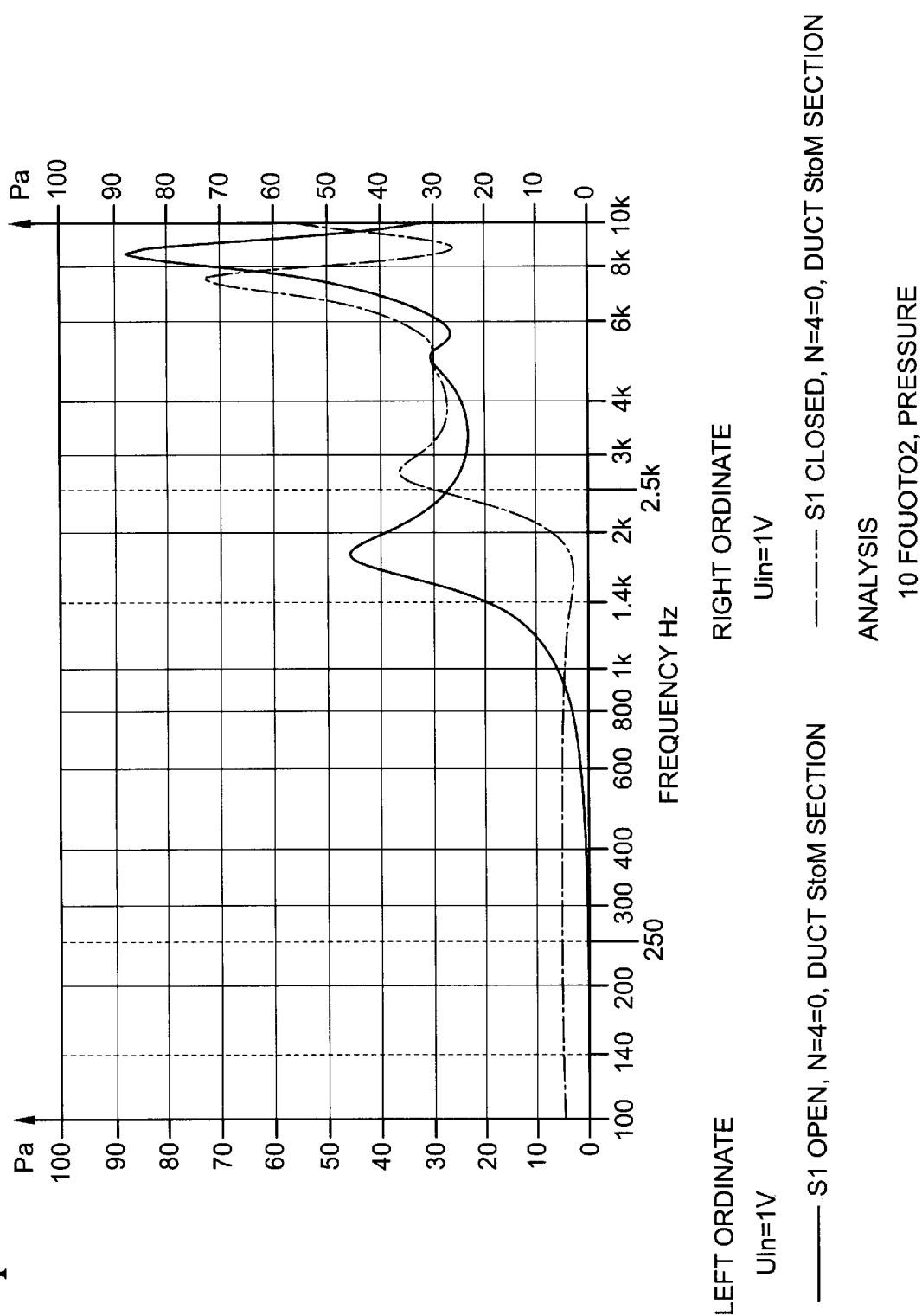
FIG. 4 is a graph illustrating the computer model output for an embodiment of the present invention.

The instrument design has been assisted by utilizing a computer model which allows evaluation of different designs for the optimization of the instrument. An acoustic model which is sold under the name of AkAbak by Panzer and Partner of Munich, Germany has been utilized. The instrument, ear canal and tympanum have been modeled as three separate acoustic entities, namely 1) lens to microphone, 2) microphone to end of tip and 3) end of tip to the tympanum including the ear canal. The graphs of FIG. 4 show a typical output from a model. The dotted curve is for the instrument when it is operated in air not sealed to the ear. The solid line is for the output when it is operated sealed to the ear. The difference in the outputs shown in the shaded areas is the response when the instrument is operated after zeroing in air. The objective is to construct the instrument to have as much difference in response between the two conditions as possible which will provide the greatest sensitivity for detecting ear abnormalities.

With reference to FIG. 1, the interior of the acoustic section of the instrument, wave guide 16 and probe tip 18, is a straight tube which is blocked off at the end away from the ear canal with a lens 22. The probe tip 18 is made of a transparent clear material which will easily transmit light. The light source 24, such as a grain of wheat light or a krypton mini lamp, is mounted in the font of the instrument so that its light will be directed onto the clear tip 18. The tip 18 transmits the light into the ear canal 36 and, in combination with the lens 22, provides a convenient and inexpensive means to view the ear canal 36 and tympanic membrane 38. The feature may ensure that there is no blockage of the acoustic energy which is projected into the car, and that the ear canal 36 is straightened to allow for the unimpeded resonance of the ear canal 36, tympanic membrane 38 and the instrument.

Figure 3A:
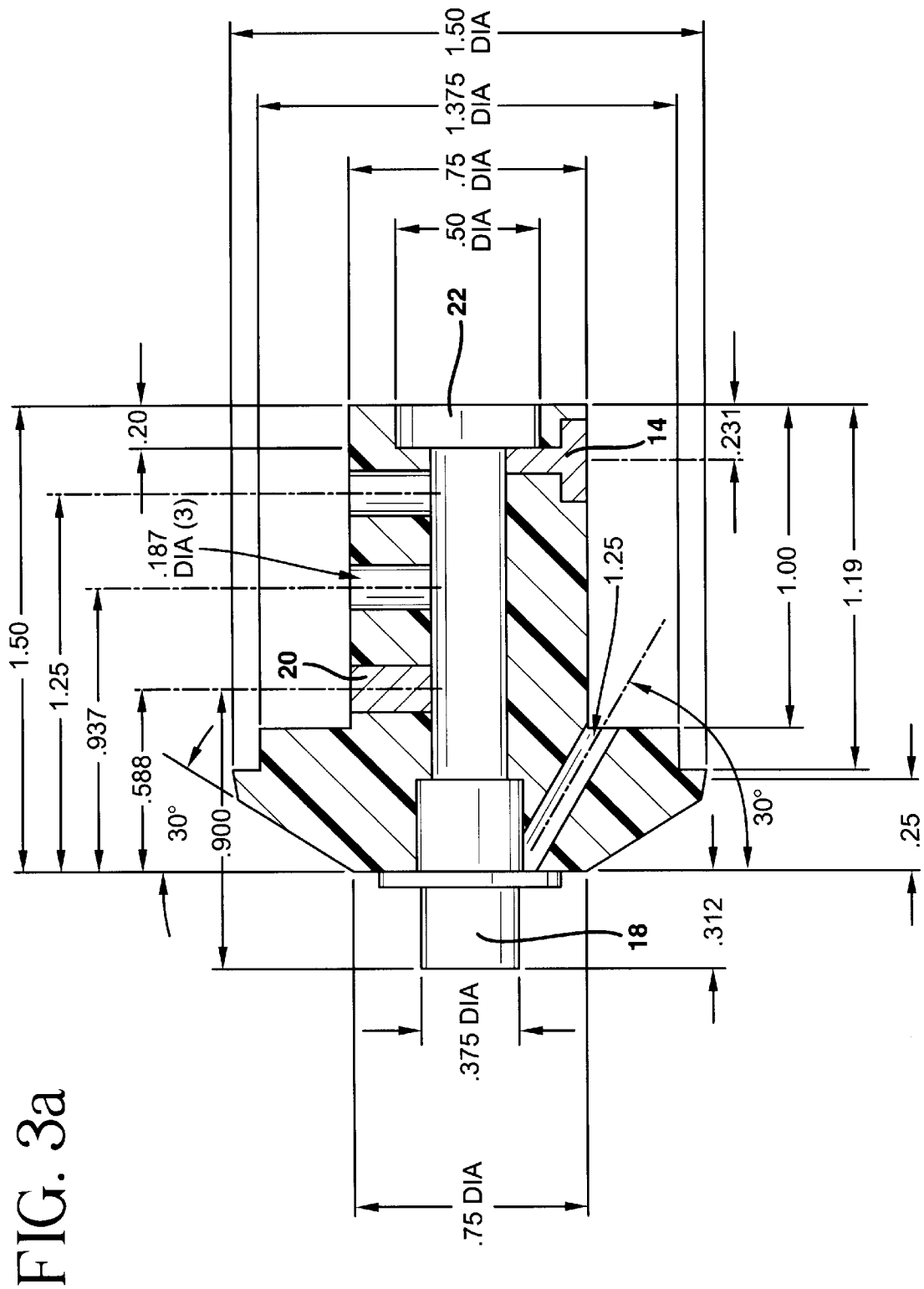
FIG. 3a is a cross-sectional view of the an embodiment of the present invention indicating the dimensions of a portion of the probe assembly.
Figure 3C:
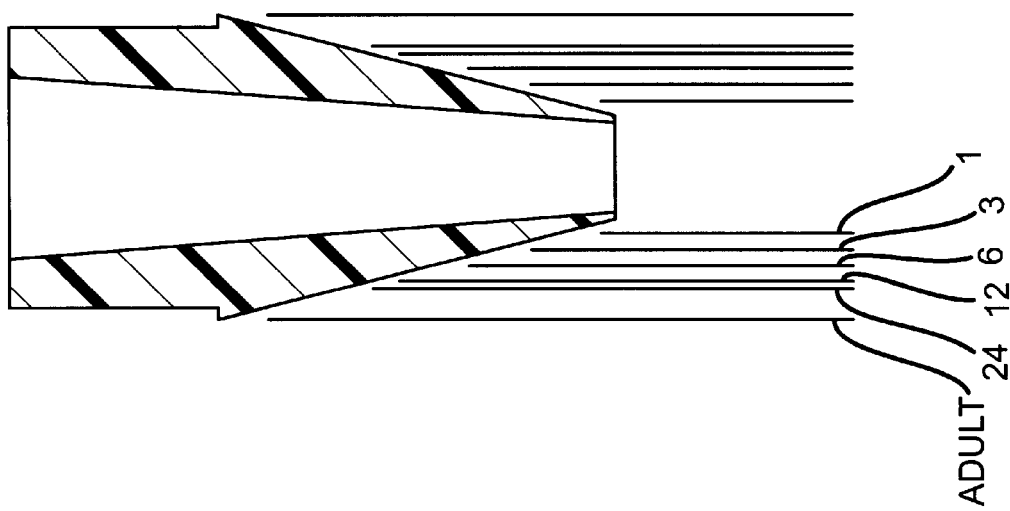
FIG. 3c is a cross-sectional view of an additional embodiment for the probe tip of the present invention.

FIG. 3a illustrates an embodiment for the portion of the housing assembly for the instrument and gives measurements for the spacing of the earphone (Acoustic Driver) 14, microscope 20 and probe tip 18. The lens 22 is mounted at the right end of this assembly. As noted, FIG. 3b shows a series of probe tip 18 designs used in the instrument. The two tips at the right hand of the drawing have worked the best since they seal in the ear canal with a good seal. The tips are made of acrylic or any other rigid and clear plastic which will transmit light. The assembly may protected with a protective covering.

FIG. 3c is a diagram of a probe tip 18 which is capable of fitting ear canals of individuals of all ages, from neonate to older child. It is the conical shape in the upper part of the drawing. FIG. 3c further contains the dimensions for ear canals from 1 month of age to adults. The dimensions for children seem to follow a proportionally progressive deepening and widening with age, thus, the distance of the instrument assembly housing to the tympanum is constant for all ages using the same tip. As a result, the resonant frequency of the total traveling wave tube will be the same for all ages. This frequency has been selected to be in the range of 2100 Hz since the ear absorbs most sound energy in this frequency range and pathologies of the ear are most easily detected at these frequencies. For example, the following table illustrates the relationships of age, and the frequency at which maximum absorption occurs:

| Age | Null Frequency (Hz) | Average Energy Reflectance (%) |
| --- | --- | --- |
| 1 mo. | 2000 | .105 |
| 3 mo. | 2000 | .120 |
| 6 mo. | 2500 | .130 |
| 12 mo. | 4000 | .160 |
| 24 mo. | 3000 | .120 |
| Adult | 3000 | .350 |

Figure 3D:
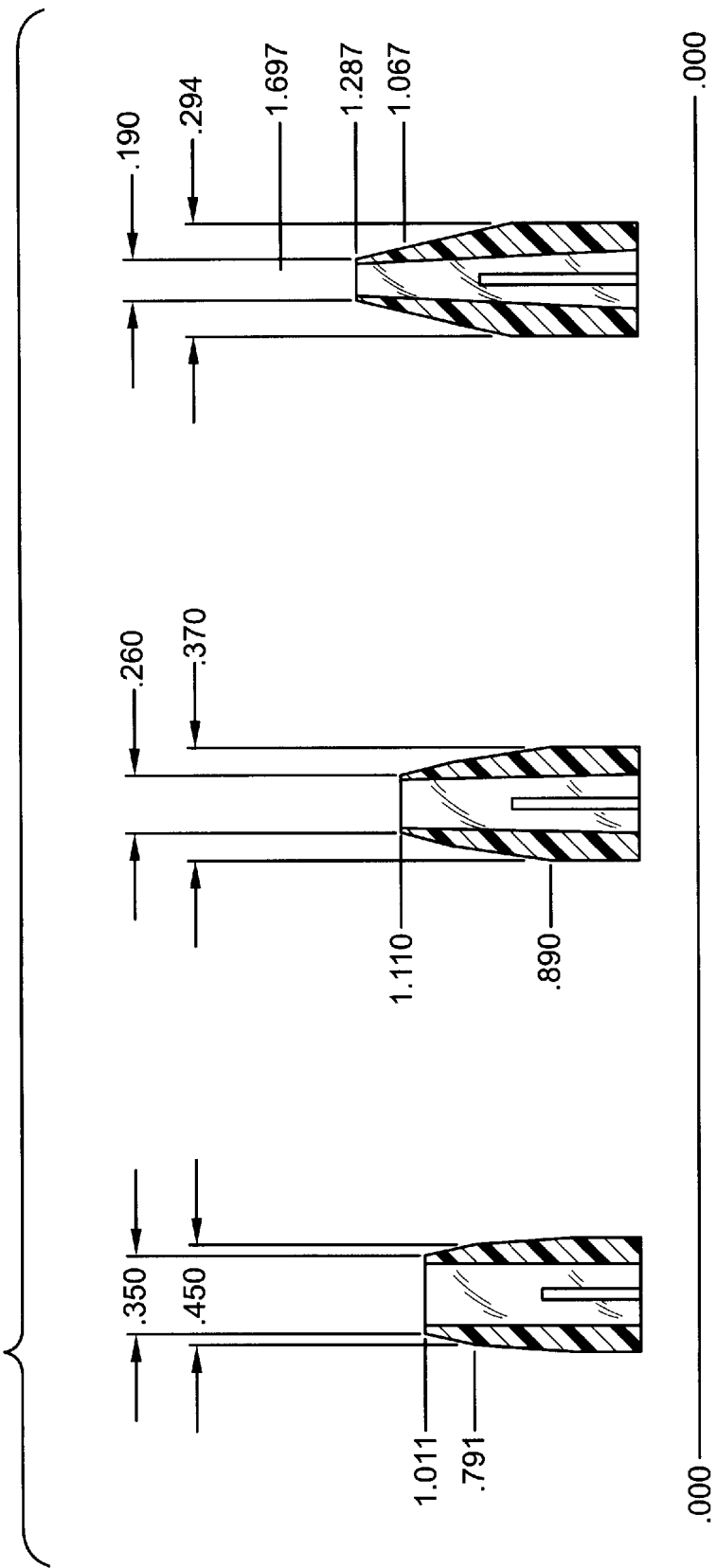
FIG. 3d shows cross-sectional views of additional embodiments for the probe tip of the present invention.

FIG. 3d shows additional embodiments of tips and their dimensions.

Figure 3E:
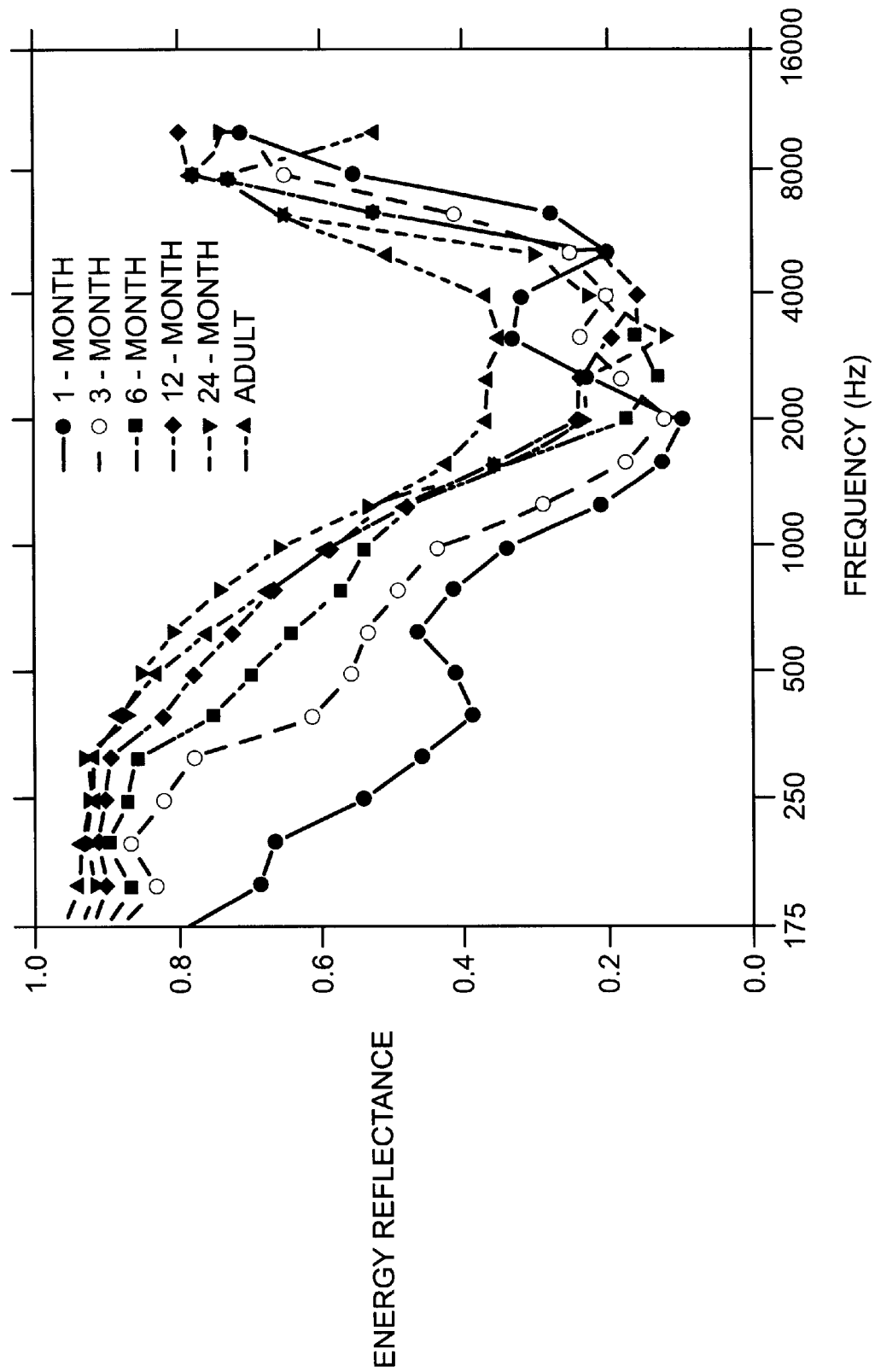
FIG. 3e is a graph illustrating the third-octave averaged energy reflectance versus center frequency (Hz) for adult group and infants of ages 1, 3, 6, 12 and 24 months.

FIG. 3e shows the null obtained when monitoring ears of children to adults tor acoustic reflection. Designing an instrument to operate in this null region will function well but it is desirable to use the lowest frequency to have an instrument of suitable length for both the acoustic and optical requirements of the application.

The acoustic driver 14 is preferably located adjacent to the lens 22. The acoustic input to the driver 14 may be pseudo-random series of pulses, commonly referred to as a Maximum Length Sequence (MLS), created either in software or using a hard wire shift register and XOR gate driven by clock pulses. The square wave pulses are selected to generate the acoustic frequencies between 100 to 10,000 Hz. The reception rate, pulse length, number of pulses, and spacing can be selected to fit the design of the unit and meet certain established criteria of frequency domain analysis for desired lowest frequency, maximum frequency and frequency resolution for the unit. The total time required for the pulse train is typically 100 msec. The length of the traveling wave guide and the ear canal determine the ¼ wave length path of the unit at the desired resonant frequency. The focal length of the lens affects the length of the resonant chamber. The frequency response of the acoustic driver and microphone also must be considered when optimizing the acoustic chamber length. The tip and instrument design are selected to give greatest sensitivity between 1,000 to 6,000 Hz with resonance falling between 1,000 to 3,500 Hz depending on the age and ear development of the subject.

Figure 3F:
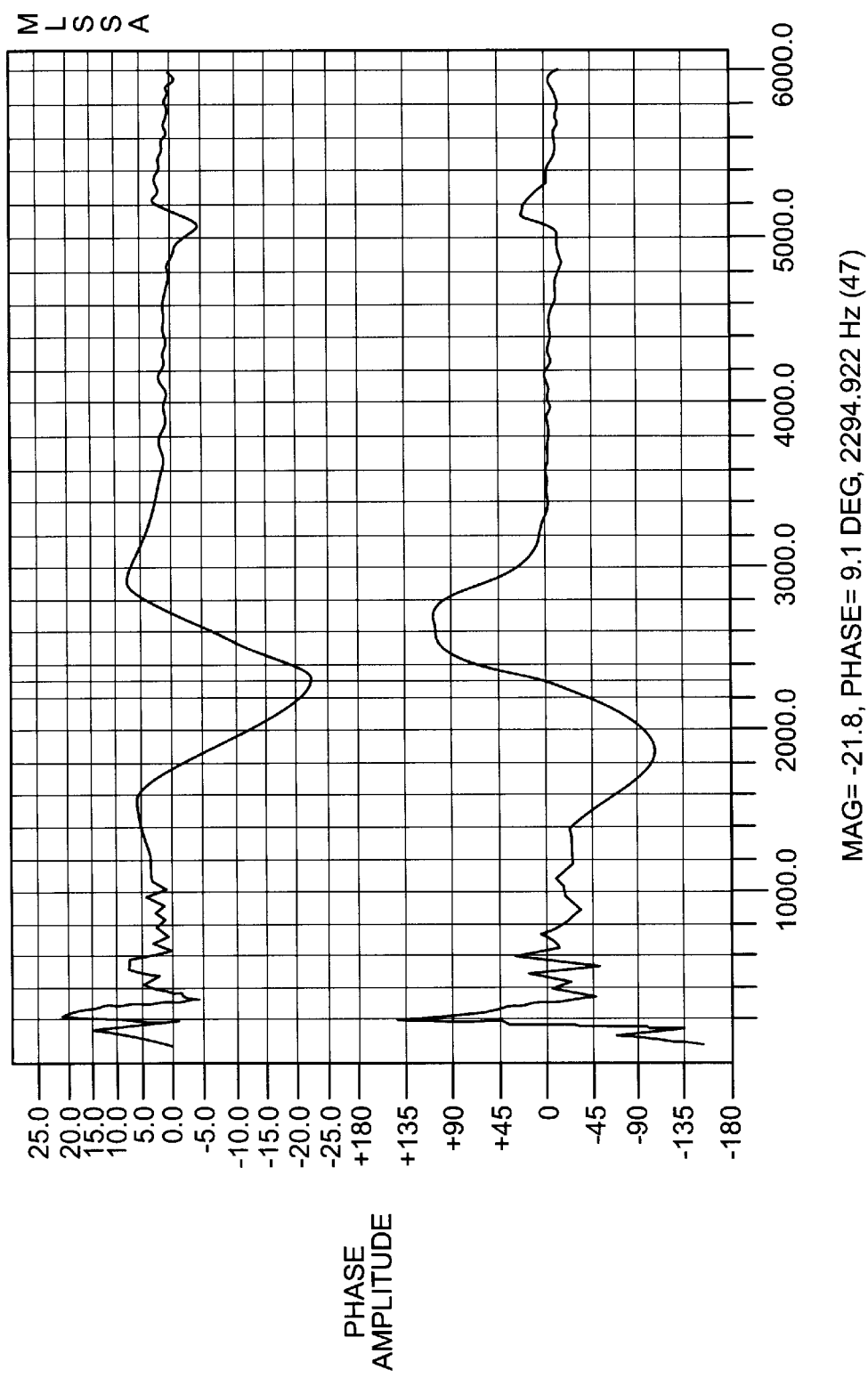
FIG. 3f is a table disclosing initial MLSSA parameters.

For development, a system called MLSSA (Maximum-Length Sequence System Analyzer) made by DRA Laboratories or Sterling, VA was utilized. This system allows the determination of the best combination of parameters for the analysis. One setup of the system is shown on Table 1 of FIG. 3f.

Valuable response data is also available at the third and fifth octaves above the resonant frequencies stated above which provide an additional potential operational frequency range for the instrument. However, the lower frequencies have been selected since the human ear has the greatest absorption of acoustic energy in this frequency range and thus any pathology of the ear will have the greatest chance of detection due to the potential percentage change which will occur between a healthy and impaired ear.

With reference to FIG. 2 the signal generator 32, preferably a pseudo-random noise generator such as a maximum length sequence (MLS) generator, drives an acoustic driver 14 through a power amplifier 34. The MLS noise enters the acoustic chamber, formed by wave guide 16 and probe tip 18, adjacent to the lens 22 and excites the chamber which includes the ear canal 36. If there is fluid in the middle ear, acoustic energy will be reflected off the tympanum 38 and back to the lens 22. The chamber and the ear canal 36 thus form a resonant closed end tube which resonates at the ½ wave length. At resonance, a null 180 degrees phase shift will be detected at the microphone 20 which is easy to distinguish with processing by computer 30 in software, with discrete circuitry or visually from a plot of amplitude and phase.

The output of the microphone 20 is fed to a computer 30. As noted, the computer 30 controls the MLS noise generator. It also performs cross-correlation of the original MLS noise and the output of the microphone, providing the impulse response of the total system. Using a Fast Fourier Transform (FFT) on the impulse response, amplitude and phase of the returned signal picked up by the microphone is derived for each analysis frequency. Before displaying the FFT, the amplitude and phase of the FFT may be equalized using a library of averaged response characteristics based on many subjects of similar age and ear responses with healthy ears. Thus, the output FFT should be flat in amplitude and phase for a healthy ear. If there is otitis media, a large differential response will be obtained as sound is reflected off the diseased tympanic membrane at the resonant frequency of the system. The output can be a plot, digital listing or other suitable output which is convenient for use by the medical practitioner.

The MLS technique has a high immunity to noise interfering with the analysis. A child can cry and useful data will still be obtained. The calibration of the instrument is based on the signal achieved when using a tube of selected dimensions to represent the worst case reflection obtainable with the instrument. The minimum signal is based on the response of healthy ears as obtained from the library referred to above. Thus, the calibration of the instrument is based on repeatable response and is not arbitrarily selected as in acoustic reflection type instruments of the past.

The instrument should be designed to resonate over a narrow frequency range so that the design and construction of the instrument can be as simple as possible to reduce manufacturing costs.

Figure 5:
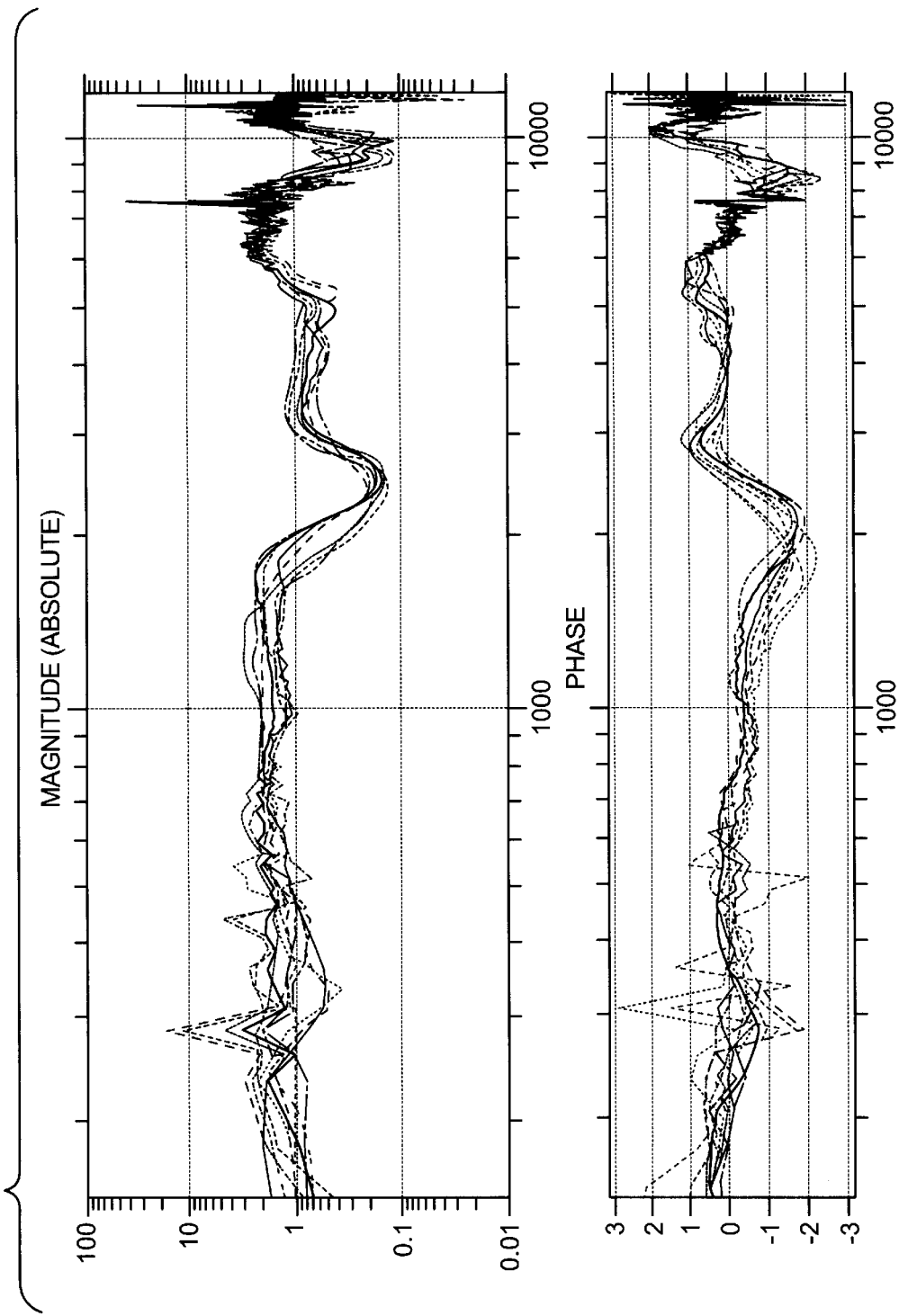
FIG. 5 are graphs illustrating the measurements of a variety of healthy ears in response to a test method of the present invention.

FIG. 5 shows the response of the library for a group of children with similar healthy ear responses. All the responses have been averaged together and stored in the processing computer. Such techniques as using the 95 confidence limits of the averaged library data can be displayed during analysis of the data to assist the practitioner in evaluating the data.

Figure 6:
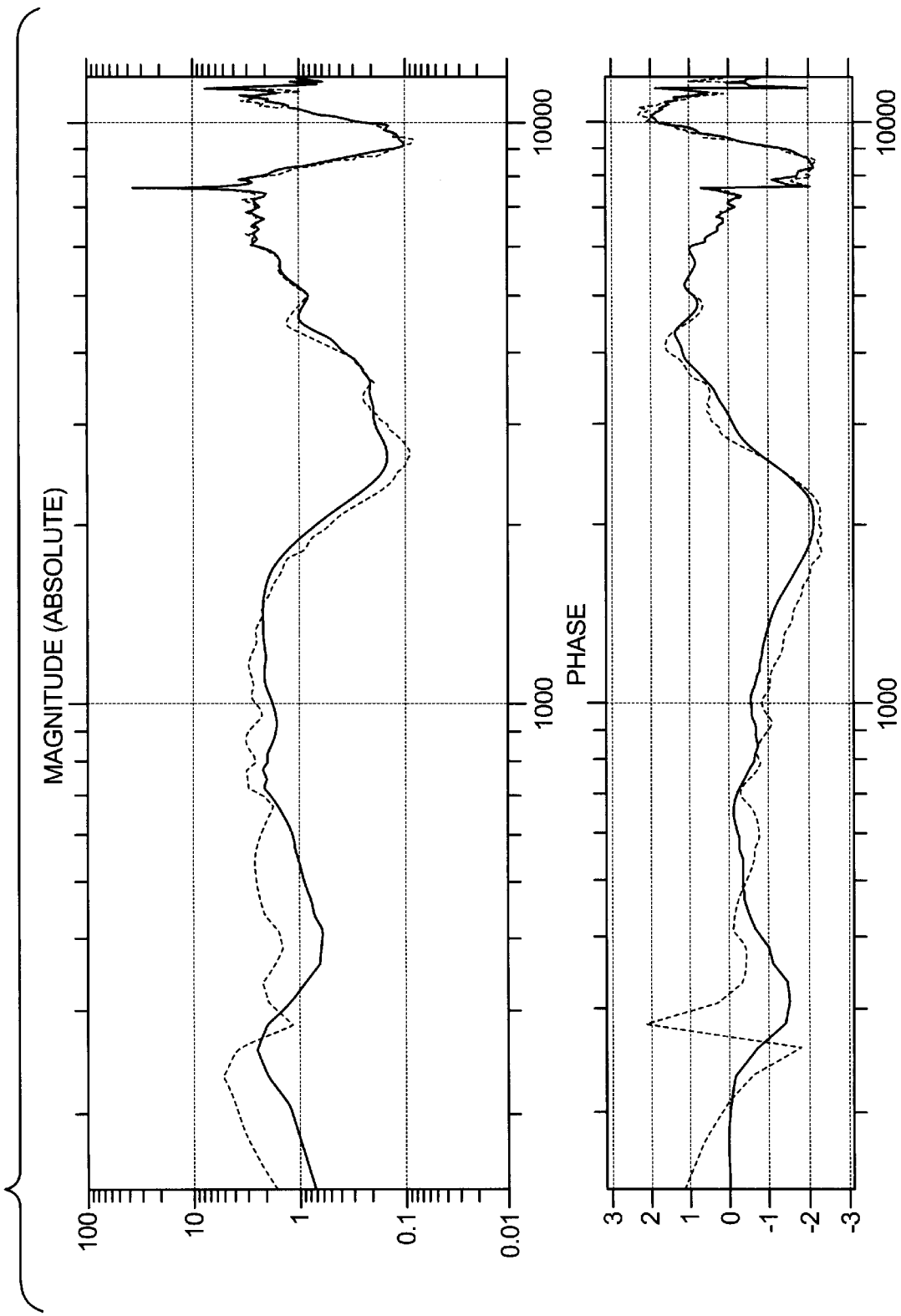
FIG. 6 are graphs illustrating the response of a child ear having an abnormal condition in response to a test method of the present invention.
Figure 7:
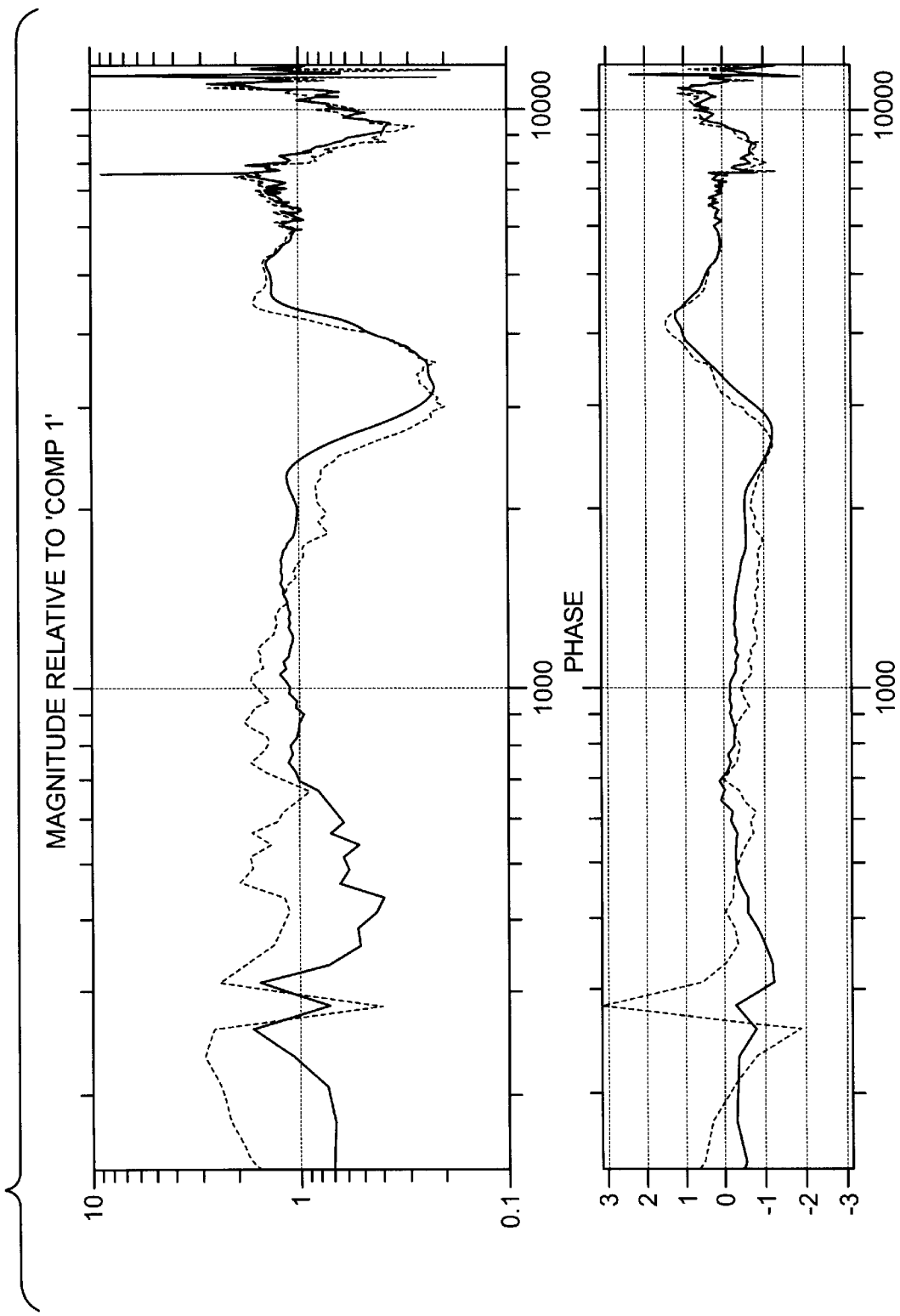
FIG. 7 are graphs illustrating the response of the child ear of FIG. 6 after removing the typical response formed from the measurements illustrated in FIG. 5.

FIG. 6 shows the response of a child with the right ear affected by otitis media. This ear shows greater reflected energy than a healthy ear but the immediate observation is less obvious than after more processing. FIG. 7 shows the dramatic improvement of the plot after the library for healthy children has been subtracted from the response as shown in FIG. 6.

Referring back to FIG. 5, the response of healthy ears for a given age range of children is shown. When using the present invention, one is able by observation or software to detect the following poor readings obtained with the instrument since the characteristic symmetrical null is not obtained:

a. If the ear canal is not straight or if there is a blockage such as ear wax, acoustic energy will be present at frequencies just above the expected resonance of the ear.

b. If the instrument tip is not scaled to the ear canal, there will be energy just below the characteristic response of the ear. In particular, there may be more than average low frequency energy components in the measurement.

c. The frequency of resonance will fall within an anticipated range for given age groups and ear development. This is used as a check on the reading. For example, when a correct tip is used, the null should appear at about 2100 Hz. An uncharacteristically high frequency at the null may indicate that the wrong tip was used.

d. The phase response of the instrument at resonance is a very good indicator of the quality of the measurement. The steeper and the straighter the slope of the phase response, the better the measurement. A regression analysis of the phase curve may provide a measure of the slope and coefficient of variation for this purpose. This is used for detecting a poor reading of the instrument.

Thus, these problems which lead to erroneous measurements can be easily detected and corrected by taking a proper measurement.

Figure 8:
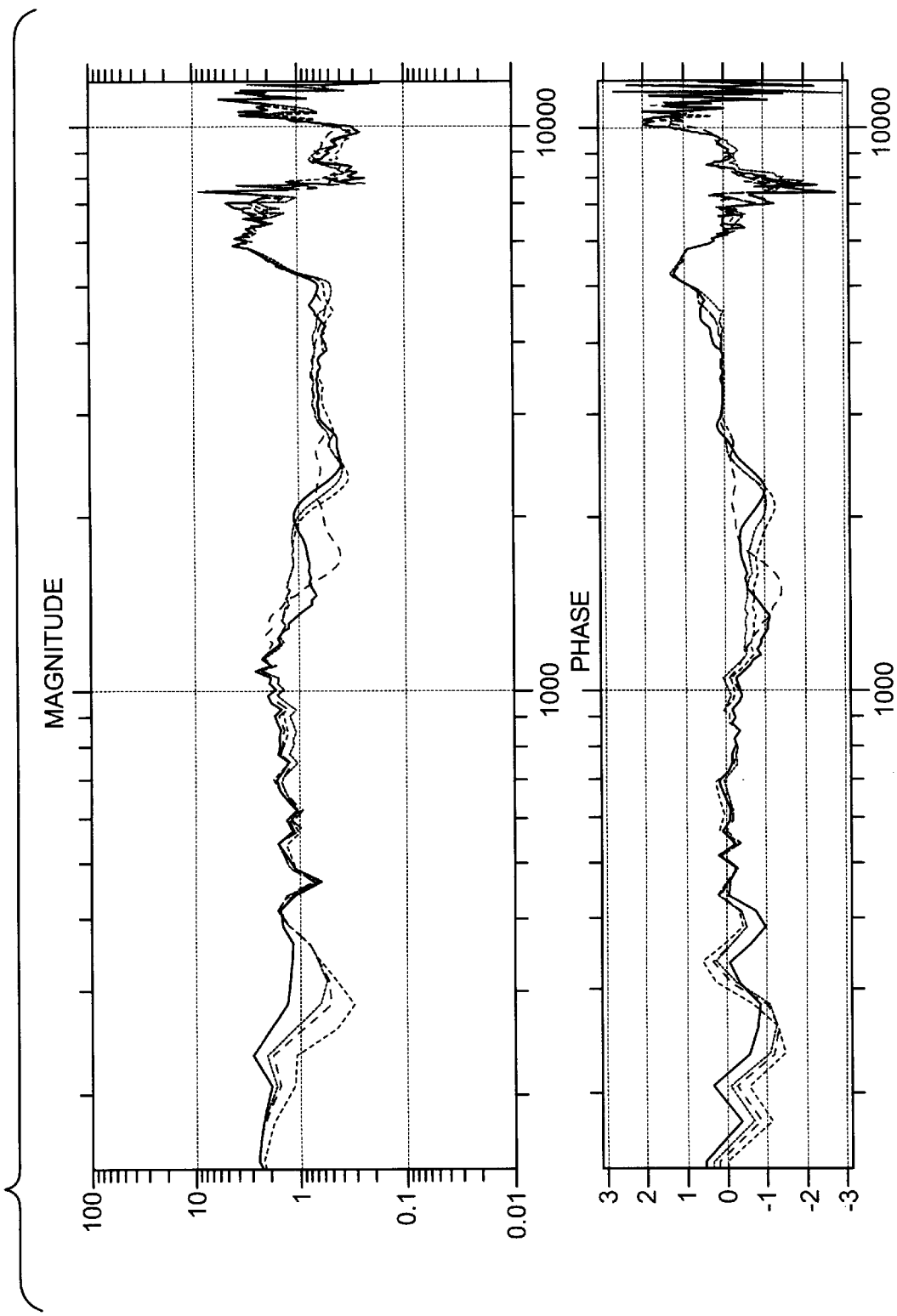
FIG. 8 are graphs illustrating the response of a child ear having a conductive hearing loss condition in response to a test method of the present invention.

FIG. 8 shows the response of a child suffering conductive hearing loss. This data has not had the library for healthy children subtracted from it. Notice the flat response in the range of 1,000 to 6,000 Hz where normally one would expect the characteristic null response. This data would show a dramatic positive response if the library for healthy children had been subtracted from it.

The present invention is measuring ear characteristics at only atmospheric pressure. Since the child's ear is operating at this pressure, it is the correct pressure to determine the response of the ear and potential impaired hearing problems. The present invention does not preclude conducting further investigations, and it may be desired to run a series of measurements over a differential pressure range of +200 to −200 mm for certain situations. For instance, if the ear is operating at other than atmospheric pressure due to otitis media, the tympanum can be pressure unloaded and tested. This method will aid in detailed analysis of the child's problem. The present invention may be further adapted to seal to the ear canal and pressurized to unload or load the tympanic membrane as desired. The response of the device in amplitude and phase also may be flattened, in both amplitude and phase, over the operating range of the device using standard techniques.

The wave guide design also may be used at ultrasonic frequencies into the megahertz region. The out of phase or in phase response of the ear canal and middle ear may be examined using ultrasonic frequencies to delineate features not detectable at lower frequencies, such as the delineation of air/fluid interfaces, which may provide more information to determine the pathology of the ear system.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims and equivalent thereto.

What I claim is:

1. An apparatus for measuring acoustic reflectance of an ear comprising:

a wave guide having a proximal and distal end;

an acoustic energy source disposed substantially at the proximal end of the wave guide and adapted to generate acoustic energy in response to a source signal comprising pseudorandom noise;

an acoustic energy detector disposed within the wave guide and adapted to generate a reflection signal in response to detection of acoustic energy;

a probe tip disposed at the distant end of the wave (guide and sized such that at least a portion penetrates an ear canal;

means for generating the source signal for the acoustic energy source;

means for receiving and processing the reflected signal from said acoustic energy detector to generate a measure of acoustic reflectance from the ear.

2. The apparatus of claim 1 further comprising a lens disposed at the proximal end of said wave guide.

3. The apparatus of claim 2 further comprising a light source disposed adjacent to the probe tip.

4. The apparatus of claim 3 wherein the probe tip is formed of a light transmissive material.

5. The apparatus of claim 1 wherein the probe tip has a substantially tapered cross-section to fit the ear canal.

6. The apparatus of claim 1 further comprising a switch adapted to control the means for receiving and processing.

7. The apparatus of claim 1 further comprising a housing for the wave guide, the acoustic energy source, the acoustic energy detector, the probe tip, the means for generating and the means for receiving and processing.

8. An apparatus for measuring acoustic reflectance of an ear, comprising:

a source of acoustic energy to apply pseudorandom noise acoustic energy to the ear;

an acoustic energy detector arranged to detect acoustic energy reflected from the ear;

means for analyzing the detected acoustic energy to provide a measure of acoustic reflectance; and an optical path allowing viewing of the ear while the source of acoustic energy applies acoustic energy to the ear.

9. The apparatus of claim 8, wherein the optical path includes a lens disposed at a proximal end of a wave guide, wherein the source of acoustic energy is disposed in said wave guide.

* * * * *